(12) United States Patent
Bergmann et al.

(10) Patent No.: US 11,293,060 B2
(45) Date of Patent: Apr. 5, 2022

(54) METHOD FOR LABELING OF ALDEHYDE CONTAINING TARGET MOLECULES

(71) Applicant: Roche Sequencing Solutions, Inc., Pleasanton, CA (US)

(72) Inventors: Frank Bergmann, Iffeldorf (DE); Ian Quang Chau, San Jose, CA (US); Peter Crisalli, Mountain View, CA (US); Hannah Marie Kallewaard-Lum, Santa Clara, CA (US); Hannes Kuchelmeister, Munich (DE); Sebastian Johannes Pomplun, Munich (DE); Hasham Saqib, San Jose, CA (US); Christian Wellner, Iffeldorf (DE)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 69 days.

(21) Appl. No.: 16/596,539

(22) Filed: Oct. 8, 2019

(65) Prior Publication Data
US 2020/0040392 A1 Feb. 6, 2020

Related U.S. Application Data

(63) Continuation of application No. PCT/US2018/027126, filed on Apr. 11, 2018.

(30) Foreign Application Priority Data

Apr. 12, 2017 (EP) .................................... 17166237

(51) Int. Cl.
| | | |
|---|---|---|
| *C12Q 1/68* | (2018.01) | |
| *C12Q 1/6869* | (2018.01) | |
| *C07D 295/13* | (2006.01) | |
| *C07D 487/04* | (2006.01) | |
| *C07H 21/02* | (2006.01) | |
| *C07H 21/04* | (2006.01) | |
| *A61K 47/68* | (2017.01) | |

(52) U.S. Cl.
CPC ......... *C12Q 1/6869* (2013.01); *C07D 295/13* (2013.01); *C07D 487/04* (2013.01); *C07H 21/02* (2013.01); *C07H 21/04* (2013.01); *A61K 47/6807* (2017.08); *C12Q 2560/00* (2013.01); *C12Q 2563/107* (2013.01); *C12Q 2563/113* (2013.01)

(58) Field of Classification Search
CPC .. C12Q 1/6869; C07D 295/13; C07D 487/04; C07H 21/02; C07H 21/04
See application file for complete search history.

(56) References Cited

FOREIGN PATENT DOCUMENTS

| | | |
|---|---|---|
| WO | 2009/150865 A1 | 12/2009 |
| WO | 2012083249 A2 | 6/2012 |
| WO | 2014/078733 A1 | 5/2014 |
| WO | 2015/148402 A1 | 10/2015 |
| WO | 2017/042038 A1 | 3/2017 |
| WO | 2018037096 A1 | 3/2018 |

OTHER PUBLICATIONS

Agarwal, Paresh et al., A Pictet-Spengler ligation for protein chemical modification, PNAS, 2013, pp. 46-51, vol. 110, No. 1.
Agarwal, Paresh et al., Hydrazino-Pictet-Spengler Ligation as a Biocompatible Method for the Generation of Stable Protein Conjugates, Bioconjugate Chemistry, 2013, pp. 846-851, vol. 24.
Carrico, Isaac S. et al., Introducing genetically encoded aldehydes into proteins, Nature Chemical Biology, 2007, pp. 321-322, vol. 3, No. 6.
Chen, Irwin et al., Site-specific labeling of cell surface proteins with biophysical probes using biotin ligase, Nature Methods, 2005, pp. 99-104, Abstract only, vol. 2.
Esser-Kahn, Aaron P. and Francis, Matthew B., Protein-Cross-Linked Polymeric Materials through Site-Selective Bioconjugation, Angewandte Chemie International Edition, 2008, pp. 3751-3754, vol. 47, No. 20.
Geoghegan, Kieran F. and Stroh, Justin G., Site-Directed Conjugation of Nonpeptide Groups to Peptides and Proteins via Periodate Oxidation of a 2-Amino Alcohol. Application to Modification at N-Terminal Serine, Bioconjugate Chemistry, 1992, pp. 138-146, vol. 3, No. 2.
Gilmore, Joshua M. et al., N-Terminal Protein Modification through a Biomimetic Transamination Reaction, Angewandte Chemie International Edition, 2006, pp. 5307-5311, vol. 45, No. 32.
Hudak, Jason E. et al., Protein Glycoengineering Enabled by the Versatile Synthesis of Aminooxy Glycans and the Genetically Encoded Aldehyde Tag, Journal of the American Chemical Society, 2011, pp. 16127-16135, vol. 133, No. 40.
Hudak, Jason E. et al., Synthesis of Heterobifunctional Protein Fusions Using Copper-Free Click Chemistry and the Aldehyde Tag, Angewandte Chemie International Edition, 2012, pp. 4161-4165, vol. 51, No. 17.
Hutchins, Benjamin M. et al., Selective Formation of Covalent Protein Heterodimers with an Unnatural Amino Acid, Chemistry & Biology, 2011, pp. 299-303, vol. 18, No. 3.
International Search Report and Written Opinion dated Aug. 3, 2018 in connection with PCT/US2018/027126 filed Apr. 11, 2018, pp. 1-15.
Kim, Chan Hyuk et al., Synthesis of Bispecific Antibodies using Genetically Encoded Unnatural Amino Acids, Journal of the American Chemical Society, 2012, pp. 9918-9921, vol. 134, No. 24.

(Continued)

*Primary Examiner* — Jezia Riley
(74) *Attorney, Agent, or Firm* — Pamela C. Ancona; Bryan Jones

(57) ABSTRACT

The present invention relates to improving the processing rate of a sequencing reaction, for example in a nanopore sequencing reaction, by means of using improved nucleoside-tags. The tags are linked to the nucleoside phosphate via a Pictet Spengler reaction. Exemplary sequencing reactions that are improved by the present methods include nanopore-based nucleic acid sequencing-by-synthesis reactions.

7 Claims, No Drawings

(56) References Cited

OTHER PUBLICATIONS

Mueller, Barbara M. et al., Antibody Conjugates with Morpholinodoxorubicin and Acid-Cleavable Linkers, Bioconjugate Chemistry, 1990, pp. 325-330, vol. 1, No. 5.

Rabuka, David et al., Site-specific chemical protein conjugation using genetically encoded aldehyde tags, Nature Protocols, 2012, pp. 1052-1067, vol. 7, No. 6.

Rashidian, Mohammad et al., Chemoenzymatic Reversible Immobilization and Labeling of Proteins without Prior Purification, Journal of the American Chemical Society, 2012, pp. 8455-8467, vol. 134, No. 20.

Rashidian, Mohammad et al., Enzymatic Labeling of Proteins: Techniques and Approaches, Bioconjugate Chemistry, 2013, pp. 1277-1294, vol. 24.

Sasaki, Tsubasa et al., N-terminal labeling of proteins by the Pictet-Spengler reaction, Bioorganic & Medicinal Chemistry Letters, 2008, pp. 4550-4553, vol. 18.

Scheck, Rebecca A. et al., Optimization of a Biomimetic Transamination Reaction, Journal of the American Chemical Society, 2008, pp. 11762-11770, vol. 130, No. 35.

Wang, Lei et al., Addition of the keto functional group to the genetic code of *Escherichia coli*, PNAS, 2003, pp. 56-61, vol. 100, No. 1.

Witus, Leah S. et al., Identification of Highly Reactive Sequences for PLP-Mediated Bioconjugation Using a Combinatorial Peptide Library, Journal of the American Chemical Society, 2010, pp. 16812-16817, vol. 132, No. 47.

Wu, Fangrui et al., Scaffold Tailoring by a Newly Detected Pictet-Spenglerase Activity of Strictosidine Synthase: From the Common Tryptoline Skeleton to the Rare Piperazino-indole Framework, Journal of the American Chemical Society, 2012, pp. 1498-1500, vol. 134.

Wu, Peng et al., Site-specific chemical modification of recombinant proteins produced in mammalian cells by using the genetically encoded aldehyde tag, PNAS, 2009, pp. 3000-3005, vol. 106, No. 9.

Yuwei He et al: "Direct Synthesis of chiral 1,2,3,4-tetrahydropyrrolo[1,2- a] pyrazines via a Catalytic Asymmetric intramolecular Aza-Friede-crafts Reaction", Organic Letters, vol. 13, No. 17, Sep. 2, 2011 (Sep. 2, 2011), pp. 4490-4493.

METHOD FOR LABELING OF ALDEHYDE CONTAINING TARGET MOLECULES

CROSS-REFERENCE TO RELATED APPLICATIONS

This is a continuation of PCT/US2018/027126, filed Apr. 11, 2018, which claims the benefit of EP 17166237.2, filed Apr. 12, 2017, the content of each of which is incorporated herein by reference in its entirety.

BACKGROUND OF THE INVENTION

Field of the Invention

The present invention relates to the use of improved tagged nucleosides in sequencing reactions, for example in nanopore based sequencing. Nucleosides are tagged by Pictet Spengler chemistry.

Brief Discussion of Related Art

Site-specific modification of proteins is a challenging problem especially with antibodies used for diagnostic or therapeutic applications. Reliable methods to site-specific polypeptide modification which are economic and applicable on industrial scale are of great importance.

Early methods of protein functionalization exploited the reactivity of either cysteine or lysine residues by reacting the protein with an excess of thiol- or amine-reactive reagents, such as maleimides or N-hydroxysuccinimidyl esters, respectively. These amino acids are abundant, widely distributed and easily modified due to availability of appropriate coupling chemistry.

However, the "lysine-labeling" strategy, when e.g. used to label antibodies or antigen-binding fragments thereof has several drawbacks: a) it often results in a significant decrease in the antigen-binding activity (lysine in or close to the antigen binding site); b) mono-labeled conjugates even at the same 1:1 stoichiometry consist of mixtures comprising a label attached via different ones of the lysines within the polypeptide and c) the yields of the desired 1:1 product are rather low.

One of the most important recent approaches for site-specific protein labeling is to incorporate bioorthogonal functionalities into proteins at specific sites via enzymatic reactions. For a recent review on "enzymatic labeling of proteins" see M. Rashidian et al., Bioconjugate Chemistry 24 (2013) 1277-1294. The enzymes used for site-specific conjugation covered in this review include formylglycine generating enzyme, sialyltransferases, phosphopantetheinyl-transferases, O-GlcNAc post-translational modification, sortagging, transglutaminase, farnesyltransferase, biotin ligase, lipoic acid ligase, and N-myristoyltransferase.

A variety of chemical, enzymatic, and genetic methods have been developed to introduce aldehydes and ketones into proteins site-specifically. These include periodate oxidation of N-terminal serine or threonine residues (Geoghegan, K. F. & Stroh, J. G., Bioconjugate Chem. (1992), 3(2):138-146; pyridoxal phosphate-mediated N-terminal transamination to yield an alpha-ketoamide or glyoxamide (Gilmore, J. M. et al., Angew. Chem. Int. Ed. (2006), 45(32):5307-5311; Scheck, R. A. et al., J. Am. Chem. Soc. (2008), 130(35):11762-11770; Witus, L. S. et al., J. Am. Chem. Soc. (2010), 132(47):16812-16817; addition of ketone-containing small molecules to protein C-terminal thioesters generated by expressed protein ligation (Esser-Kahn, A. P. & Francis, M. B. Angew. Chem. Int. Ed. (2008), 47(20):3751-3754); genetically encoded incorporation of unnatural amino acids containing ketones via amber stop codon suppression (Wang, L., et al., Proc. Natl. Acad. Sci., USA, (2003), 100(1):56-61; Hutchins, B. M., et al., Chem. Biol. (2011), 18(3):299-303; Kim, C. H., et al., J. Am. Chem. Soc. (2012), 134(24):9918-9921); genetic encoding of peptide tags that direct enzymatic ligation of aldehyde- or ketone-bearing small molecules (Rashidian, M., et al., J Am. Chem. Soc. (2012), 134(20):8455-8467; Chen, I., et al., Nat. Methods (2005) 2(2):99-104); and genetic encoding of a site for modification by the formylglycine generating enzyme (FGE), the "aldehyde tag" method developed by Carrico and Bertozzi (Carrico, I. S., et al., Nat. Chem. Biol. 3(6):321-322; Wu, P. et al., Proc. Natl. Acad. Sci. USA (2009), 106:3000-3005; Hudak, J. E., et al., J Am. Chem. Soc. (2011), 133(40):16127-16135; Hudak, J. E., et al. (2012), Chem. Int. Ed. (2012), 51(17):4161-4165; Rabuka, D. et al., Nat. Protoc. (2012), 7(6):1052-1067).

The diversity of methods for introducing reactive carbonyl groups into proteins stands in contrast to the limited number of reactions that have been widely adopted for their chemical modification. The vast majority of reports use the hydrazone and oxime-forming reactions mentioned above, due to their bioorthogonality, operational simplicity (i.e., no auxiliary reagents are required), and good yields under mild aqueous conditions. Unfortunately, the resulting C=N bonds are susceptible to hydrolysis (Mueller, B. M., et al., Bioconjugate Chem. (1990), 1(5):325-330) leading to instability. However, longterm stability would be required for many routine applications.

Indole compounds substituted at the beta-position have been described by T. Sasaki, et al., Bioorg. Med. Chem. Lett. (2008), 18:4550-4553). In WO 2009/150865 a method is disclosed for producing a modified protein by using the Pictet-Spengler reaction. Heterocyclic indole derivatives substituted at their beta-C position are described and in the examples exclusively indole derivatives substituted at their beta-C position are used and shown. The group of Bertozzi described indole aminooxy or hydrazine functionality to increase reactivity (P. Agarwal, et al., PNAS (2013), 110 (1), 46-51; P. Agarwal, et al., Bioconjugate Chem. (2013), 24 (6), 846-851; WO 2014/078733) in a Pictet-Spengler type of reaction.

It has now surprisingly been found that compounds based on N-(2-aminoethyl)pyrrole, wherein the amino-ethyl is attached via the nitrogen of the pyrrole ring and further comprising a desired moiety of interest can be used in a Pictet-Spengler type reaction with great advantages, e.g., in terms of reaction kinetics and yield. In addition the conjugates (compounds) obtained by this method are disclosed as well as certain N-(2-aminoethyl)pyrrole substances.

SUMMARY OF THE INVENTION

The present invention discloses a method for binding to a target molecule comprising an aldehyde a compound derived from N-(2-aminoethyl)pyrrole, which compound also comprises a moiety of interest. More specifically it relates to a method of producing a compound according to Formula II, the method comprising; reacting a compound of Formula I with a target T comprising an aldehyde group as given below Formula I:

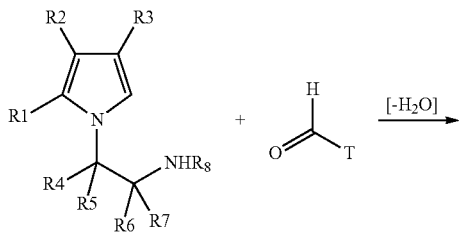

thereby obtaining a compound (=conjugate) according to Formula II,

Formula II:

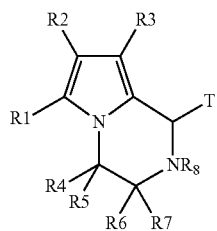

wherein R1, R2 and R3 independently are H, substituted or unsubstituted alkyl, substituted or unsubstituted alkenyl, substituted or unsubstituted heteroalkyl, substituted or unsubstituted aryl, or substituted or unsubstituted heteroaryl, wherein R4, R5, R6, R7 and R8 independently are H, substituted or unsubstituted alkyl, substituted or unsubstituted heteroalkyl, substituted or unsubstituted aryl, substituted or unsubstituted heteroaryl, or -LM, wherein two of R4, R5, R6, R7, and R8 optionally are linked to form a substituted or unsubstituted cycloalkyl or a substituted or unsubstituted heterocycloalkyl, wherein L is absent or is a linker, wherein M is a moiety of interest, and wherein T is a target molecule, with the proviso that at least one of R4, R5, R6, R7 or R8 is -LM.

Further disclosed are the conjugates obtained by the method disclosed herein, comprising both the target molecule T and the moiety of interest M, e.g., a compound according to Formula II, Formula II

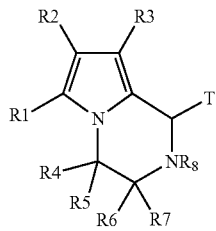

wherein R1, R2, R3, R4, R5, R6, R7, R8 and T are as defined above.

Further disclosed are substances according to Formula III,

Formula III:

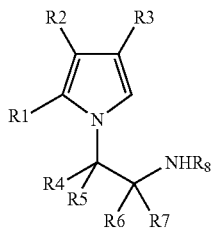

wherein R1, R2 and R3 independently are H, substituted or unsubstituted alkyl, substituted or unsubstituted alkenyl, substituted or unsubstituted heteroalkyl, substituted or unsubstituted aryl, or substituted or unsubstituted heteroaryl, wherein R4, R5, R6 and R7 independently are H, substituted or unsubstituted alkyl, substituted or unsubstituted heteroalkyl, substituted or unsubstituted aryl, substituted or unsubstituted heteroaryl, or -LM, wherein R8 is H, substituted or unsubstituted alkyl, substituted or unsubstituted heteroalkyl, substituted or unsubstituted aryl, or substituted or unsubstituted heteroaryl, wherein two of R4, R5, R6, R7, and R8 optionally are linked to form a substituted or unsubstituted cycloalkyl or a substituted or unsubstituted heterocycloalkyl, wherein M is a moiety of interest selected from the group consisting of a nucleotide, an oligonucleotide, a peptide, a label, a cytotoxic agent, a partner of a binding pair and a maleimide, wherein the linker L is selected from substituted or unsubstituted alkyl, substituted or unsubstituted heteroalkyl, or an oligopeptide and may comprise an amide linkage, an ester linkage, an alkene or a triazole, with the proviso that at least one of R4, R5, R6 or R7 is -LM.

DETAILED DESCRIPTION OF THE INVENTION

The present invention discloses a generic method for binding to a target molecule comprising an aldehyde a compound derived from N-(2-aminoethyl)pyrrole, which compound also comprises a moiety of interest.

In one embodiment the present disclosure relates to a method of producing a compound according to Formula II, the method comprising; reacting a compound of Formula I with a target T comprising an aldehyde group as given below Formula I:

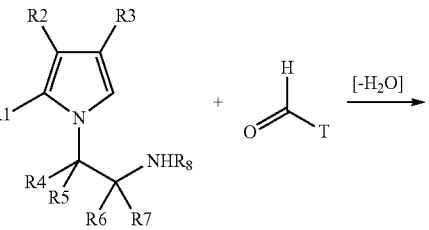

thereby obtaining a compound according to Formula II,

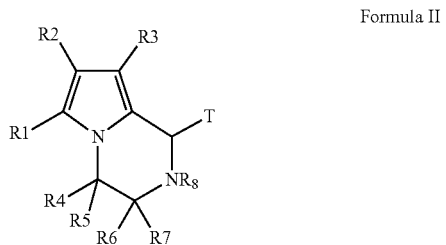

Formula II wherein R1, R2 and R3 independently are H, substituted or unsubstituted alkyl, substituted or unsubstituted alkenyl, substituted or unsubstituted heteroalkyl, substituted or unsubstituted aryl, or substituted or unsubstituted heteroaryl, wherein R4, R5, R6, R7 and R8 independently are H, substituted or unsubstituted alkyl, substituted or unsubstituted heteroalkyl, substituted or unsubstituted aryl, substituted or unsubstituted heteroaryl, or -LM, wherein two of R4, R5, R6, R7, and R8 optionally are linked to form a substituted or unsubstituted cycloalkyl or a substituted or unsubstituted heterocycloalkyl, wherein L is absent or is a linker, wherein M is a moiety of interest, and wherein T is a target molecule, with the proviso that at least one of R4, R5, R6, R7 or R8 is -LM.

The word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include plural referents, unless the content clearly dictates otherwise.

As used herein, including the accompanying claims, the substituents have the meanings commonly known to the skilled person.

The term "alkyl" by itself or as part of another substituent, means, unless otherwise stated, a straight or branched chain, or cyclic hydrocarbon radical, or combination thereof, having the number of carbon atoms designated (i.e. C1-C20 means one to twenty carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, and the like. In certain embodiments alkyl is a linear or branched alkyl chain with a length of 1-20 carbon atoms, or with a length of 1-10 carbon atom, or with a length of 1-6 carbon atoms. In one embodiment, alkyl is methyl or ethyl.

The term "aryl" and "heteroaryl" by itself or as part of another substituent, means, unless otherwise stated, an aromatic ring system (i.e. a 5 or 6 membered ring) which may also be fused with additional aromatic ring systems (preferably from 1 to 4 rings). The "heteroaryl" ring system comprises 1-4 heteroatoms selected from O, S and N. Examples of "aryl" include, but are not limited to, groups such as phenyl and naphthyl. Examples of "heteroaryl" include, but are not limited to, groups derived from furane, thiophene, pyrrole, imidazole, triazole and indole.

As the skilled artisan appreciates, chemical entities like alkyl or aryl—just to mention two non-limiting examples—may be "substituted", i.e. one or more hydrogen(s) may be replaced/substituted. In one embodiment a hydrogen is substituted by a group selected from haloalkyl (e.g., —CF3 and —CH2CF3) and acyl (e.g., —C(O)CH3, —C(O)CF3, —C(O)CH2OCH3, substituted or unsubstituted alkyl, substituted or unsubstituted heteroaryl, substituted or unsubstituted heterocycloalkyl, —OR', =O, —NRR", —SR', -halogen, —C(O)OR', —C(O)NR'R", —OC(O)NR'R", —NR"C(O)R', —NR'—C(O)NR"R'", —NR"C(O)OR', —S(O)R', —S(O)2R', —S(O)2NR'R", —NRS(O)2R', —CN, halogen and —NO2, —N3, —CH(Ph)2, fluoro(C1-C4)alkoxy, and fluoro(C1-C4)alkyl, wherein R, R" and R'" are preferably independently selected from hydrogen and substituted or unsubstituted alkyl. Preferred substituents are alkyl like methyl or ethyl, aryl like phenyl or benzyl, methoxy or ethoxy, an amine like dimethylamino, carboxylic acid derivatives like carboxylic acid, ester or amides, and nitro, cyano, azide and halogen.

The term "heteroalkyl" by itself or in combination with another term, means a stable straight or branched chain, or cyclic hydrocarbon radical, or combinations thereof, consisting of the number of carbon atoms stated under "alkyl" above and at least one heteroatom selected from the group consisting of O, N, P and S. The heteroatom(s) may be placed at any interior position of the heteroalkyl group or at the end position, i.e. opposite to the position via which the heteroalkyl group is attached to the remainder of the molecule. The heteroatom(s) may also be positioned between the pyrrole ring of the N-(2-aminoethyl)pyrrole core structure and the (hetero)alkyl or (hetero)aryl substituent. Preferably, each heteroatom being a member of a chain or cyclus at an interior position is flanked by carbon atoms. Heteroatoms at interior positions may be unsubstituted, e.g. carry a hydrogen atom, or may have at least one substituent selected from the group consisting of alkyl and O. Examples of heteroalkyl include, but are not limited to, —CH2—CH2—O—CH3, —CH2—CH2—NH—CH3, —CH2—CH2—N(CH3)—CH3, —CH2—S—CH2—CH3, —CH2—CH2—S(O)—CH3, —CH2—CH2—S(O)2—CH3, —O—CH3, —O—CH2—CH3, —NH—CH3, —NH—CH2-CH3, —N(CH3)2, —N(CH2—CH3)2 and poly(alkylene oxide), especially polyethylene glycol (PEG) derivatives.

The term "alkenyl" describes chemical groups that are but for the presence of at least one double bond, otherwise as defined under alkyl above.

The term "heteroalkenyl" describes chemical groups that are but for the presence of at least one double bond, otherwise as defined under heteroalkyl above.

In one embodiment R1, R2 and R3 independently are H or methyl.

In one embodiment R1, R2 and R3 all are H.

As the person skilled in the art will appreciate a "linker" is any appropriate structure providing for an attachment between two moieties with any desired distance. The two moieties thus are not bound directly to each other but via such linking structure or linker.

The linker L as comprised in Formula I or II, respectively, in one embodiment may be defined by its backbone length and in one embodiment has a backbone length of between 1 and 100 atoms. In one embodiment L has a backbone length of between 1 and 50 atoms. In one embodiment, L is a straight or branched saturated, unsaturated, unsubstituted, or substituted C1-C50 alkyl chain, or a 1 to 50 atom chain with a backbone consisting of carbon atoms and one or more heteroatoms selected from O, N and S, or a 1 to 50 atom chain with a backbone consisting of carbon atoms and one or more heteroatoms selected from O, N and S comprising at least one aryl, heteroaryl, substituted aryl or substituted heteroaryl group (wherein e.g. a phenylene ring accounts for a length of four atoms). In one embodiment the linker L in a compound according to the present invention is a saturated C1-C20 alkyl chain, or a 1 to 20 atom chain with a backbone consisting of carbon atoms and one or more heteroatoms selected from O, N and S, or a 1 to 20 atom chain with a backbone consisting of carbon atoms and one or more heteroatoms selected from O, N and S comprising at least one aryl, heteroaryl, substituted aryl or substituted heteroaryl group (wherein e.g. a phenylene ring accounts for a length of four atoms).

In one embodiment the linker L, as comprised in a compound of Formula I or Formula II, respectively, is absent or selected from substituted or unsubstituted alkyl, substituted or unsubstituted heteroalkyl, or an oligopeptide and may comprise or consist of an amide linkage, an ester linkage, an alkene or a triazole. In one embodiment L is selected from substituted or unsubstituted alkyl, substituted or unsubstituted heteroalkyl, or an oligopeptide and may comprise or may consist of an amide linkage, an ester linkage, an alkene or a triazole.

In one embodiment the linker L, as comprised in the definitions for a compound of Formula I or Formula II, respectively, is absent.

In one embodiment the linker L, as comprised in a compound of Formula I or Formula II, respectively, is selected from substituted or unsubstituted alkyl, substituted or unsubstituted heteroalkyl, or an oligopeptide and may comprise or may consist of an amide linkage, an ester linkage, an alkene or a triazole. In one embodiment L, as comprised in a compound of Formula I or Formula II, respectively, is selected from substituted or unsubstituted alkyl, substituted or unsubstituted heteroalkyl, an amide bond and an oligopeptide.

In one embodiment L, as comprised in a compound of Formula I or Formula II, respectively, is selected from substituted or unsubstituted alkyl and substituted or unsubstituted heteroalkyl.

The peptide that may be comprised in L in one embodiment is an oligopeptide and consists of between 2 and 20 amino acids.

In one embodiment L, as comprised in a compound of Formula I or Formula II, respectively, is bound to the moiety of interest M via an ester, an ether, a thioether, an amine, an amide, a disulfide, a carbonate, a carbamate, an alkene, a triazole, a dihydropyridazine or a phosphodiester bond.

In one embodiment the "moiety of interest" (M) as comprised in a compound of Formula I or of Formula II, respectively, and used in a method as disclosed herein, is selected from the group consisting of a nucleotide, an oligonucleotide, a peptide, i.e., an oligopeptide, or a polypeptide, a label, a cytotoxic agent, a partner of a binding pair and a functional group.

In one embodiment the moiety of interest M, comprised in a compound of Formula I or Formula II, respectively, is of low molecular weight, i.e., it has less than 20000 Dalton in molecular weight. In further embodiments the moiety of interest has a molecular weight of between 100 and 15000, of between 100 and 10000, of between 100 and 5000 and of between 100 and 2000 Dalton.

The peptide that may represent the moiety of interest M used in a method disclosed herein, in one embodiment consists of between 1 and 100 amino acids.

In one embodiment only one of either the linker L or the moiety of interest M is an oligopeptide or a peptide, respectively.

The oligonucleotide that may represent the moiety of interest M used in a method disclosed herein, in one embodiment consists of between 2 and 100 nucleotides.

In one embodiment the moiety of interest M comprises a nucleotide.

One of the moieties of interest M, comprised in a compound of Formula I or Formula II, respectively, is a label. Any label which can be covalently attached to the linker (L) can be used. The label may function to: (i) provide a detectable signal; (ii) interact with a second label to modify the detectable signal provided by the first or second label, e.g. to give FRET (fluorescence resonance energy transfer); (iii) affect mobility, e.g. electrophoretic mobility or cell-permeability, by charge, hydrophobicity, shape, or other physical parameters, or (iv) provide a capture moiety, e.g. to modulate ionic complexation.

Numerous labels (also referred to as dyes) are available which can be generally grouped into the following categories:

(a) Fluorescent Dyes

Fluorescent dyes are e.g. described by Briggs et al "Synthesis of Functionalized Fluorescent Dyes and Their Coupling to Amines and Amino Acids," J. Chem. Soc., Perkin-Trans. 1 (1997) 1051-1058).

Fluorescent labels or fluorophores include rare earth chelates (europium chelates), fluorescein type labels including FITC, 5-carboxyfluorescein, 6-carboxyfluorescein; rhodamine type labels including TAMRA, lissamine, Texas Red; dansyl; cyanines; phycoerythrins; and analogues thereof. The fluorescent labels can be conjugated to an aldehyde group comprised in the target molecule using the techniques disclosed herein. Fluorescent dyes and fluorescent label reagents include those which are commercially available, e.g., from Invitrogen/Molecular Probes (Eugene, Oreg., USA), ThermoFisher Scientific (Waltham, Mass., USA) and Pierce Biotechnology, Inc. (Rockford, Ill.).

(b) Luminescent Dyes

Luminescent dyes or labels can be further subcategorized into chemiluminescent and electrochemiluminescent dyes.

The different classes of chemiluminogenic labels include luminol, acridinium compounds, coelenterazine and analogues, dioxetanes, systems based on peroxyoxalic acid and their derivatives. For immunodiagnostic procedures predominantly acridinium based labels are used (a detailed overview is given in Dodeigne C. et al., Talanta 51 (2000) 415-439).

The labels of major relevance used as electrochemiluminescent labels are the Ruthenium- and the Iridium-based electrochemiluminescent complexes, respectively. Electrochemiluminescense (ECL) proved to be very useful in analytical applications as a highly sensitive and selective method. It combines analytical advantages of chemiluminescent analysis (absence of background optical signal) with ease of reaction control by applying electrode potential. In general Ruthenium complexes, especially [Ru (Bpy)3]2+ (which releases a photon at ~620 nm) regenerating with TPA (Tripropylamine) in liquid phase or liquid-solid interface are used as ECL-labels. Recently also Iridium-based ECL-labels have been described (WO2012107419(A1)).

(c) Radioactive labels make use of radioisotopes (radionuclides), such as 3H, 11C, 14C, 18F, 32P, 35S, 64Cu, 68Gn, 86Y, 89Zr, 99TC, 111In, 123I, 124I, 125I, 131I, 133Xe, 177Lu, 211At, or 131Bi.

(d) Metal-chelate complexes suitable as labels for imaging and therapeutic purposes are well-known in the art (US 2010/0111856; U.S. Pat. Nos. 5,342,606; 5,428,155; 5,316, 757; 5,480,990; 5,462,725; 5,428,139; 5,385,893; 5,739, 294; 5,750,660; 5,834,456; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61 (2001) 4474-4482; Mitchell, et al, J. Nucl. Med. 44 (2003) 1105-1112; Kobayashi et al Bioconjugate Chem. 10 (1999) 103-111; Miederer et al, J. Nucl. Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al, J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-20).

One of the moieties of interest M, comprised in a compound of Formula I or Formula II, respectively, is a cytotoxic agent. In one embodiment the moiety of interest is a cytotoxic agent selected from: (i) chemotherapeutic agents, which may function as microtubule inhibitors, mitosis inhibitors, topoisomerase inhibitors, or DNA intercalators; (ii) protein toxins, which may function enzymatically; and (iii) therapeutic radioisotopes. In one embodiment the moiety of interest is a chemotherapeutic agent.

Exemplary chemotherapeutic agents include, but are not limited to, a maytansinoid, an auristatin, a dolastatin, a trichothecene, CC1065, a calicheamicin and other enediyne antibiotics, a taxane, an anthracycline, and stereoisomers, isosters, analogues or derivatives thereof.

Protein toxins include diphtheria-A chain, non-binding active fragments of diphtheria toxin, exotoxin A chain (from *Pseudomonas aeruginosa*), ricin A chain (Vitetta et al (1987) Science, 238:1098), abrin A chain, modeccin A chain, alphasarcin, *Aleurites fordii* proteins, dianthin proteins, *Phytolaca americana* proteins (PAPI, PAPII, and PAP-5), *Momordica charantia* inhibitor, curcin, crotin, *Sapaonaria officinalis* inhibitor, gelonin, mitogellin, restrictocin, phenomycin, enomycin, and the tricothecenes (WO 93/21232).

Therapeutic radioisotopes include 32P, 33P, 90Y, 125I, 131I, 131In, 153Sm, 186Re, 188Re, 211At, 212B, 212Pb, and radioactive isotopes of Lu.

The radioisotope may be incorporated in known ways (Fraker et al (1978) Biochem. Biophys. Res. Commun. 80: 49-57; "Monoclonal Antibodies in Immunoscintigraphy" Chatal, CRC Press 1989). Carbon-14-labeled 1-isothiocyanatobenzyl-3-methyldiethylene triamine pentaacetic acid (MX-DTPA) is an exemplary chelating agent for conjugation of a radionuclide to the complex (WO 94/11026).

As mentioned above, one of the possible moieties of interest M, comprised in a compound of Formula I or Formula II, respectively, is a partner of a binding pair.

A binding pair as used herein consists of two partners binding to each other with high affinity, i.e. with one nanomolar affinity or better. As the skilled artisan will readily appreciate, M as comprised in a compound of Formula I or Formula II, respectively, represents one of two possible partner elements, e.g., the hapten of a hapten/anti-hapten binding pair. Embodiments for binding pairs are for example the binding pairs consisting of receptor and ligand, hapten and anti-hapten antibody, and binding pairs based on naturally occurring high affinity binding pairs. In certain embodiments the partner of a binding pair is a ligand or a hapten, or it is one partner of a naturally occurring high affinity binding pair.

One example of a receptor-ligand binding pair is a pair consisting of a steroid hormone receptor and the corresponding steroid hormone. In one embodiment the ligand is a steroid hormone.

In one embodiment the partner of a binding pair is a hapten, or it is one partner of a naturally occurring high affinity binding pair.

Examples of binding pairs based on naturally occurring high affinity binding pairs representing one embodiment according to the present invention are biotin or biotin analogues such as aminobiotin, iminobiotin or desthiobiotin and avidin or streptavidin as well as the FimG and DsF binding pair. The biotin-(strept)avidin binding pair is well-known in the art. The basic principles of the FimG-DsF binding pair are e.g. described in WO2012/028697.

One other type of a binding pair and embodiment of the present invention is a hapten and anti-hapten antibody binding pair. A hapten is an organic molecule with a molecular weight of 100 to 2000 Dalton. In one embodiment the hapten has a molecular weight of 100 to 1000 Dalton. Usually an organic molecule of such molecular weight is not immunogenic or of comparatively low immunogenicity. A hapten can be rendered immunogenic by coupling it to a carrier molecule and anti-hapten antibodies can be generated according to standard procedures. In one embodiment the hapten may be selected from the group comprising sterols, bile acids, sexual hormones, corticoids, cardenolides, cardenolide-glycosides, bufadienolides, steroid-sapogenines and steroid alkaloids, cardenolides and cardenolide-glycosides. Representatives of these substance classes are digoxigenin, digitoxigenin, gitoxigenin, strophanthidin, digoxin, digitoxin, ditoxin, strophanthin. An additional suitable hapten is for example fluorescein.

As obvious to the skilled artisan some substances, e.g. biotin or its analogues, are both; partners of naturally occurring binding pairs, or haptens, i.e. they can be use to generate antibodies binding thereto.

In one embodiment the moiety of interest M, comprised in a compound of Formula I or Formula II, respectively, is a functional group selected from the group consisting of carboxylic acid, carboxylic acid ester, epoxide, N-hydroxysuccinimide ester, amino group, halogen, hydrazine, hydroxyl, sulfhydryl, maleimido, alkenyl, alkynyl, azide, isocyanate, isothiocyanate, phosphoramidite, trans-cyclooctene, and tetrazine.

In one embodiment the moiety of interest M, comprised in a compound of Formula I or Formula II, respectively, is a functional group selected from the group consisting of carboxylic acid, N-hydroxysuccinimide ester, amino group, halogen, sulfhydryl, maleimido, alkynyl, azide, isocyanate, isothiocyanate and phosphoramidite.

In one embodiment the moiety of interest M, comprised in a compound of Formula I or Formula II, respectively, is a partner of a binding pair.

In one embodiment moiety of interest M, comprised in a compound of Formula I or Formula II, respectively, is selected from the group consisting of a nucleotide, an oligonucleotide, a fluorescent or a luminescent label, a cytotoxic agent, biotin or a biotin analogue, digoxin or a digoxin analogue, and maleimide.

A preferred digoxin analogue is digoxigenin.

In one embodiment the moiety of interest M, comprised in a compound of Formula I or Formula II, respectively, is selected from hapten, biotin or biotin analogues such as aminobiotin, iminobiotin or desthiobiotin, FimG, ligand and oligonucleotide.

In one embodiment the moiety of interest M, comprised in a compound of Formula I or Formula II, respectively, is selected from hapten and biotin or biotin analogues such as aminobiotin, iminobiotin or desthiobiotin.

In one embodiment the moiety of interest M, comprised in a compound of Formula I or Formula II, respectively, is biotin or a biotin analogue such as aminobiotin, iminobiotin or desthiobiotin.

In one embodiment the moiety of interest M, comprised in a compound of Formula I or Formula II, respectively, is biotin.

Biotin analogues are aminobiotin, iminobiotin or desthiobiotin.

As the skilled artisan appreciates, a nucleotide is a compound that consist of a ribose or deoxyribose sugar joined to a purine or pyrimidine base and to a phosphate group which e.g. are the basic structural units of nucleic acids (such as RNA and DNA). Nucleotides may be modified at the sugar, the base or the phosphate part, for example they may be modified at the C5-position of the pyrimidine base. Preferred examples are 5'-phosphates or polyphosphates of 2'-deoxyadenosine, 2'-deoxyguanosine, 2'-deoxycytidine and 2'-deoxythymidine. Other nucleotide analogues or derivatives are described further below in the detailed description on oligonucleotides (nucleic acids).

An oligonucleotide is composed of multiple nucleotides which are connected via phosphate ester linkages and may also comprise non-nucleotidic building blocks as for example spacer molecules like glycol, 1,3-propanediol, dSpacer® from Glen Research or Chemgenes, or even aromatic building blocks like substituted benzenes, as long as they can be incorporated into an oligonucleotide. Some of the nucleotide(s) comprised in such oligonucleotide may be substituted with other functional groups such as labeling moieties (e.g. biotin, fluorescein).

In one embodiment the oligonucleotide representing the moiety of interest M consists of between 2 and 50 subunits selected from nucleotides and non-nucleotidic building blocks.

In one embodiment the moiety of interest M as comprised in a compound of Formula I or of Formula II, respectively, and used in a method as disclosed herein, has a molecular weight of less than 20000 Dalton and is a functional group, a partner of a binding pair, a cytotoxic agent or a label.

In one embodiment the moiety of interest M, comprised in a compound of Formula I or Formula II, respectively, has a molecular weight of 100 to 20000 Dalton and is selected from the group consisting a partner of a binding pair and a label.

As indicated above the method disclosed herein is of great utility in binding any kind of target molecule T comprising an aldehyde group to a compound of Formula I.

In one embodiment the target molecule T is selected from the group consisting of a solid phase, a polypeptide, a protein, a carbohydrate, a nucleotide and a nucleic acid.

A "solid phase", "solid support" or "solid surface" is typically glass or a polymer, the most commonly used polymers being cellulose, polyacrylamide, nylon, polystyrene, polyvinyl chloride, or polypropylene. As the skilled artisan will appreciate a solid phase can either by its nature contain an aldehyde functionality or can be chemically modified to introduce an aldehyde group. As further evident, a solid phase can be coated with any of a polypeptide, a protein, a carbohydrate, a nucleotide and a nucleic acid, which for the purpose of the present invention comprise an aldehyde group. The solid supports may be in the form of tubes, beads, or discs of microplates. In one embodiment the solid phase is a paramagnetic bead based on glass or any of the above mentioned polymers.

In one embodiment the target molecule T is selected from the group consisting of a polypeptide, a protein, a carbohydrate, a nucleotide and a nucleic acid.

A "carbohydrate" is a biological molecule consisting of carbon (C), hydrogen (H) and oxygen (O) atoms, usually with a hydrogen-oxygen atom ratio of 2:1 (as in water); in other words, with the empirical formula $Cm(H2O)n$ (where m usually is the same as n). Some exceptions exist (m is different from n); for example, deoxyribose, a sugar component of DNA, has the empirical formula $C5H10O4$. Carbohydrates are technically hydrates of carbon; structurally it is more accurate to view them as polyhydroxy aldehydes and ketones.

The term carbohydrate is most common in biochemistry, where it is a synonym of 'saccharide', a group of molecules that includes sugars, starch, and cellulose. In one embodiment the carbohydrate is selected from sugars, starch, and cellulose.

In one embodiment the target molecule T is selected from the group consisting of a polypeptide, a protein, and a nucleic acid.

In one embodiment the target molecule T is selected from the group consisting of a protein, and a nucleic acid.

In one embodiment the target molecule T is a polypeptide or a protein.

The terms "peptide", "oligopeptide", "polypeptide" and "protein" are known to the person skilled in the art and further defined herein below.

In general the term "peptide" refers to a polymer comprising two or more amino acids (=amino acid residues) in which the monomers of amino acids are joined together through amide bonds Amino acids may be either the D- or L-isomer thereof and a polypeptide may be either composed of D-isomers or of L-isomers of amino acids. In one embodiment a peptide consists of L-isomers of amino acids. The term peptide comprises both oligopeptides and polypeptides.

The term "oligopeptides" is used for peptides comprising at least 2 and at most 20 amino acids.

The term "polypeptides" is used for peptides comprising at least 21 amino acids. Naturally occurring polypeptides are composed of naturally occurring amino acids. Additionally, polypeptides can be synthesized comprising unnatural amino acids, for example, β-alanine, phenylglycine, or/and homoarginine. Polypeptides may undergo so-called secondary modifications, like phosphorylation or glycosylation. Such modified polypeptides are also polypeptides according to the present invention. In one embodiment the polypeptide used in a method according to the present disclosure has between 21 and 1000 amino acid residues.

In the context of the different aspects of present invention, the term "protein" refers to a molecule comprising one or more peptide chains that resume a secondary and tertiary structure and additionally refers to a protein that is made up of several peptide chains, i.e. several subunits, forming a quaternary structure. A protein has sometimes non-peptide groups attached, which can be called prosthetic groups or cofactors. A protein may also comprise secondary modifications, e-g., a phosphorylation, a glycosylation, etc.

In one embodiment, in the target molecule T comprising an aldehyde group, the aldehyde group is introduced by the formyl-generating enzyme (FGE) methodology. In brief, formylglycine generating enzyme recognizes a pentapeptide consensus sequence, CxPxR, and it specifically oxidizes the cysteine in this sequence to a formylglycine. The FGE recognition sequence or aldehyde tag can be inserted into heterologous recombinant proteins produced in either prokaryotic or eukaryotic expression systems (see e.g. Rabuka et al, Nature Protocols 2012, 7, 1052-1067). In another embodiment an N-terminal glycine can be converted to an aldehyde by a transamination reaction (see e.g. Gilmore et al, Angew. Chem. Int. Ed. Engl. 2006, 45, 5307). In other embodiments, for example, an N-terminal serine or threonine may be oxidized to an aldehyde, and glycostructures of a sugar-modified protein may be oxidized with periodate to produce aldehyde groups.

In one embodiment the target molecule T is a polypeptide or a protein selected from a polypeptide partner of a binding pair and an antibody.

The polypeptide partner of a binding pair for example is the receptor in a receptor ligand binding pair, avidin or streptavidin of the biotin avidin or streptavidin binding pair, or the FimG of the FimG/DsF binding pair.

In one embodiment the target molecule T as used in a method according to the present disclosure is a polypeptide or a protein selected from FimG, avidin, streptavidin and an antibody.

In one embodiment the target molecule T as used in a method according to the present disclosure is a polypeptide or a protein selected from avidin, streptavidin and an antibody.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light-chain and heavy-chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The subunit structures and three-dimensional configurations of different classes of immunoglobulins are well known and described generally in, for example, Abbas et al., Cellular and Mol. Immunology, 4th ed., W.B. Saunders, Co. (2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen-binding region thereof. Examples of antibody fragments include Fab, Fab', F(ab')2, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields a F(ab')2 fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody-hinge region. Fab'-SH is the designation herein for Fab' in which the cysteine residue(s) of the constant domains bear a free thiol group. F(ab') 2 antibody fragments originally were produced as pairs of Fab' fragments which have hinge cysteines between them. Other chemical couplings of antibody fragments are also known.

"Single-chain Fv" or "scFv" antibody fragments comprise the VH and VL domains of an antibody, wherein these domains are present in a single polypeptide chain. Generally, the scFv polypeptide further comprises a polypeptide linker between the VH and VL domains that enables the scFv to form the desired structure for antigen binding. For a review of scFv, see, e.g., Plueckthun, In: The Pharmacology of Monoclonal Antibodies, Vol. 113, Rosenburg and Moore (eds.), Springer-Verlag, New York (1994) pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 0404 097; WO 1993/01161; Hudson, P. J. et al., Nat. Med. 9 (2003) 129-134; and Holliger, P. et al., PNAS USA 90 (1993) 6444-6448. Triabodies and tetrabodies are also described in Hudson, P. J. et al., Nat. Med. 9 (2003) 129-134.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

As mentioned above, in one embodiment the target molecule T as used in a method according to the present disclosure is selected from the group consisting of a solid phase, an oligopeptide, a polypeptide, a protein, a carbohydrate, a nucleotide and a nucleic acid.

In one embodiment the target molecule T as used in a method according to the present disclosure is a nucleic acid.

The term "oligonucleotide" or "nucleic acid" as used herein, generally refers to short, generally single stranded, polynucleotides that comprise at least 2 nucleotides and at most about 1000 nucleotides. In a preferred embodiment an oligonucleotide will have a length of at least 9, 10, 11, 12, 15, 18, 21, 24, 27 or 30 nucleotides. In a preferred embodiment an oligonucleotide will have a length of no more than 200, 150, 100, 90, 80, 70, 60, 50, 45, 40, 35 or 30 nucleotides. In one embodiment the oligonucleotides comprise the natural nucleosides 2'-deoxyadenosine (dA), 2'-deoxyguanosine (dG), 2'-deoxycytidine (dC), 2'-deoxythymidine (dT), adenosine, guanosine, cytidine and uridine, and 2'-deoxyuridine (dU). In another embodiment the nucleic acid may be double-stranded.

The term oligonucleotide or nucleic acid is to be understood broadly and includes DNA and RNA as well as analogues and modification thereof. A nucleic acid analogue may for example contain a substituted nucleotide carrying a substituent at the standard bases adenine, guanine, cytosine, thymine, uracil. Examples of such nucleosides comprising substituted nucleobases are: 5-substituted pyrimidines like 5 methyl dC, aminoallyl dU or dC, 5-(aminoethyl-3-acrylimido)-dU, 5-propinyl-dU or -dC, 5 halogenated-dU or -dC; N substituted pyrimidines like N4-ethyl-dC; N substituted purines like N6-ethyl-dA, N2-ethyl-dG; 8 substituted purines like 8-[(6-amino-hex-1-yl)-amino]-dG or -dA, 8 halogenated dA or dG, 8-alkyl dG or dA; and 2 substituted dA like 2 amino dA.

A nucleic acid analogue may contain a nucleotide or a nucleoside analogue. I.e. the naturally occurring nucleobases can be exchanged by using nucleobase analogues like 5-nitroindol d riboside; 3 nitro pyrrole d riboside, deoxyinosine (dI), deoxyxanthosine (dX); 7 deaza-dG, -dA, -dI or -dX; 7-deaza-8-aza-dG, -dA,-dI or -dX; 8-aza-dA, -dG, -dI or -dX; d formycin; pseudo dU; pseudo iso dC; 4 thio dT; 6 thio dG; 2 thio dT; iso dG; 5-methyl-iso-dC; N8-linked 8-aza-7-deaza-dA; 5,6-dihydro-5-aza-dC; and etheno-dA or pyrrolo-dC. As obvious to the skilled artisan, the nucleobase in the complementary strand has to be selected in such manner that duplex formation is specific. If, for example, 5-methyl-iso-dC is used in one strand (e.g. (a)) iso dG has to be in the complementary strand (e.g. (a')).

In a nucleic acid analogue the oligonucleotide backbone may be modified to contain substituted sugar residues, sugar analogues, modifications in the internucleoside phosphate moiety, and/or be a PNA.

An oligonucleotide may for example contain a nucleotide with a substituted deoxy ribose like 2'-methoxy, 2'-fluoro, 2'-methylseleno, 2'-allyloxy, 4'-methyl dN (wherein N is a nucleobase, e.g., A, G, C, T or U).

Sugar analogues are for example xylose; 2',4' bridged ribose like (2'-O, 4'-C methylene)-bridged ribose (oligomer known as LNA) or (2'-O, 4'-C ethylene)-bridged ribose (oligomer known as ENA); L-ribose, L-d-ribose, hexitol (oligomer known as HNA); cyclohexenyl (oligomer known as CeNA); altritol (oligomer known as ANA); a tricyclic ribose analogue where C3' and C5' atoms are connected by an ethylene bridge that is fused to a cyclopropane ring (oligomer known as tricycloDNA); glycerol (oligomer known as GNA); glucopyranose (oligomer known as homo-DNA); carbaribose (with a cyclopentan instead of a tetrahydrofuran subunit); hydroxymethyl-morpholine (oligomers known as morpholino DNA).

A great number of modifications comprising a modified internucleosidic phosphate moiety are also known not to interfere with hybridization properties and such backbone modifications can also be combined with substituted nucleotides or nucleotide analogues. Examples are phosphorthioate, phosphorodithioate, phosphoramidate and methylphosphonate oligonucleotides.

PNA (having a backbone without phosphate and d-ribose) can also be used as a DNA analogue. The above mentioned modified nucleotides, nucleotide analogues as well as oligonucleotide backbone modifications can be combined as desired in an oligonucleotide in the sense of the present invention.

In case the nucleic acid or oligonucleotide shall be used as target molecule T, in certain embodiments, an aldehyde modification can be incorporated by chemical or enzymatical means. By chemical means, formyl modified phosphoramidites (e.g. formylindole phosphoramidite, Glen Research) may be used to introduce an aldehyde group, also NHS ester chemistry may be applied. Aldehyde modified nucleoside triphosphates may be used to incorporate aldehyde groups enzymatically.

In a method according to the present disclosure the various embodiments given above for the moiety of interest M, as comprised in a compound of Formula I, as well as for the target moiety T can be combined. For example, in one embodiment the moiety of interest M, as comprised in a compound of Formula I, is selected from the group consisting of a nucleotide, an oligonucleotide, a fluorescent or a luminescent label, a cytotoxic agent, biotin or a biotin analogue, digoxin or a digoxin analogue, and maleimide and the target molecule T is a polypeptide or a protein, e.g. an antibody. In another example the moiety of interest M, comprised in a compound of Formula I, is a nucleotide and the target molecule T is a nucleic acid.

In one embodiment the moiety of interest M, comprised in a compound of Formula I, is an oligonucleotide and the target molecule T is a nucleotide. In one embodiment the moiety of interest M, comprised in a compound of Formula I, is an oligonucleotide and the target molecule T is an oligonucleotide.

In one embodiment the target molecule T comprises multiple, i.e 2 to 50, aldehyde groups. As a result, when practicing the method disclosed herein, multiple moieties of interest M are connected with the target molecule T.

Also disclosed herein are the conjugates obtained by the method described and disclosed in the present invention, comprising both the target molecule T and the moiety of interest M.

In one embodiment the present disclosure relates to a compound (or a conjugate) according to Formula II, Formula II:

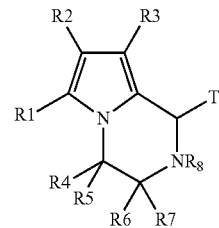

wherein R1, R2, R3, R4, R5, R6, R7, R8 and T all are as defined above under Formula I. I.e. at least one of R4, R5, R6, R7 or R8 is -LM, with L and M as defined above. As the skilled artisan appreciates a compound of Formula II is the product obtained upon practicing the method disclosed herein. In a compound of Formula II a target molecule T is bound, or as the person in the art also says is conjugated, via the core structure of Formula II, 1,2,3,4-tetrahydropyrrolo[1,2-a]pyrazine, to a moiety of interest M.

In a method according to the present disclosure the various embodiments for a target molecule T on the one hand and various moieties of interest M on the other hand can be combined as desired. These options for combinations result in a large variety of conjugates with significant utility in various fields of use.

In one embodiment a compound (conjugate) of Formula II, comprising an antibody as target molecule and a fluorescent label or a luminescent label, or biotin or a biotin analogue, digoxin or a digoxin analogue, as moiety of interest is produced. In one embodiment such compound is used in an immunological detection method.

In one embodiment a compound (conjugate) of Formula II, comprising an antibody as target molecule and a cytotoxic agent as moiety of interest is produced. In one embodiment such compound is used for therapeutic purposes, e.g. in anti-cancer therapy.

In one embodiment a compound (conjugate) of Formula II, comprising a nucleotide as target molecule and an oligonucleotide as moiety of interest is produced. In one embodiment such compound is used for next generation sequencing approaches, e.g. in nanopore sequencing.

Further disclosed are substances according to Formula III,

Formula III

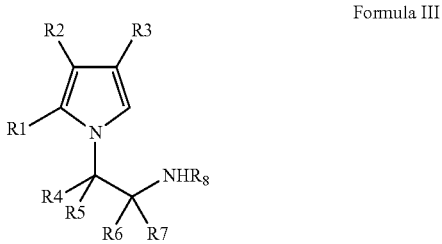

wherein R1, R2 and R3 independently are H, substituted or unsubstituted alkyl, substituted or unsubstituted alkenyl, substituted or unsubstituted heteroalkyl, substituted or unsubstituted aryl, or substituted or unsubstituted heteroaryl, wherein R4, R5, R6 and R7 independently are H, substituted or unsubstituted alkyl, substituted or unsubstituted heteroalkyl, substituted or unsubstituted aryl, substituted or unsubstituted heteroaryl, or -LM, wherein R8 is H, substituted or unsubstituted alkyl, substituted or unsubstituted heteroalkyl, substituted or unsubstituted aryl, or substituted or unsubstituted heteroaryl, wherein two of R4, R5, R6, R7, and R8 optionally are linked to form a substituted or unsubstituted cycloalkyl or a substituted or unsubstituted heterocycloalkyl, wherein M is a moiety of interest selected from the group consisting of a nucleotide, an oligonucleotide, a peptide, a label, a cytotoxic agent, a partner of a binding pair and a maleimide, wherein the linker L is selected from substituted or unsubstituted alkyl, substituted or unsubstituted heteroalkyl, or an oligopeptide and may comprise an amide linkage, an ester linkage, an alkene or a triazole, with the proviso that at least one of R4, R5, R6 or R7 is -LM.

One important difference between a compound of Formula I and a substance of Formula III, respectively, is the fact that R8 of Formula III is not -LM.

In one embodiment R1, R2 and R3 in the substance of Formula III independently are H or methyl.

In one embodiment R1, R2 and R3 in the substance of Formula III all are H.

As indicated above, the linker L, as comprised in the substance of Formula III, is selected from substituted or unsubstituted alkyl, substituted or unsubstituted heteroalkyl, or an oligopeptide and may comprise an amide linkage, an ester linkage, an alkene or a triazole. Except for these limitations the linker L as comprised in a substance according to Formula III meets the definitions as described above for the linker L as comprised in the compounds of Formula I and Formula II, respectively.

In one embodiment L, as comprised in the substance of Formula III, is selected from substituted or unsubstituted alkyl, and substituted or unsubstituted heteroalkyl, and may comprise or consist of an amide linkage, an ester linkage, an alkene or a triazole.

In one embodiment L, as comprised in the substance of Formula III, is selected from substituted or unsubstituted alkyl, substituted or unsubstituted heteroalkyl and an oligopeptide.

In one embodiment L, as comprised in the substance of Formula III, is selected from substituted or unsubstituted alkyl and substituted or unsubstituted heteroalkyl.

The linker L as comprised in Formula III, may be further defined by its backbone length and in one embodiment has a backbone length of between 1 and 100 atoms.

The "moiety of interest" (M), as comprised in the substance of Formula III, is selected from the group consisting of a nucleotide, an oligonucleotide, a peptide, a label, a cytotoxic agent, a partner of a binding pair and a functional group. Except for these limitations the moiety of interest M as comprised in a substance according to Formula III meets the definitions as described above for the moiety of interest M as comprised in the compounds of Formula I and Formula II, respectively.

If the moiety of interest M, as comprised in the substance of Formula III, is a nucleotide, an oligonucleotide, a peptide, a label, a cytotoxic agent, a partner of a binding pair or a functional group all these moieties are as defined above.

In one embodiment the moiety of interest, as comprised in a substance of Formula III, is selected from the group consisting of a nucleotide, an oligonucleotide, a fluorescent or a luminescent label, a cytotoxic agent, biotin or a biotin analogue, digoxin or a digoxin analogue, and maleimide.

The nucleotide, the oligonucleotide, the fluorescent label, the luminescent label, the cytotoxic agent, biotin or the biotin analogue, digoxin or the digoxin analogue comprised as moiety of interest M in the substance of Formula III all are as defined above.

In one embodiment the moiety of interest, as comprised in a substance of Formula III, is selected from the group consisting of a luminescent label, a cytotoxic agent, and biotin or a biotin analogue.

In one embodiment the moiety of interest, as comprised in a substance of Formula III, is a nucleotide or an oligonucleotide.

As demonstrated in the Examples section, the pyrrole compounds substituted at their N position, as disclosed in both Formula I and Formula III, respectively, show higher reactivity than C-substituted pyrrole compounds. In addition, the conjugation products (substances according to Formula II) obtained by reacting a target molecule comprising an aldehyde and the pyrrole compounds according to the present disclosure, which are substituted at the N-position of the pyrrole ring, also revealed higher stability.

Example 1

Synthesis of (1): Boc-N-Pyrrolo-alanine (2-((tert-butoxycarbonyl)amino)-3-(1H-pyrrol-1-yl)propanoic Acid)

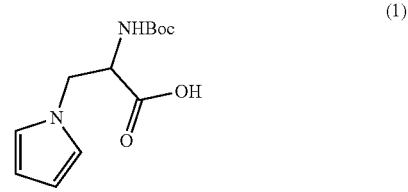 [SMILES: CC(C)(C)OC(=O)NC(Cn1cccc1)C(=O)O]

(1)

Synthesized according to procedure from Chemical Science, 6(4), 2219-2223; 2015

1H NMR (400 MHz, DMSO-d6) δ=12.93-12.78 (m, 1H), 7.18-7.07 (m, 1H), 6.74-6.66 (m, 2H), 6.06-5.84 (m, 2H), 4.31-3.91 (m, 3H), 1.32 (s, 9H)

Example 2

Synthesis of (2): Fmoc-N-Pyrrolo-alanine-OH

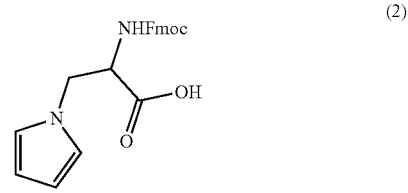

(2)

Boc-N-Pyrrolo-alanine (1) (150 mg, 0.591 mmol) was dissolved in CH2Cl2/TFA (3 mL, 1:1) and stirred at room temperature for 1 h. After this time the solvent was removed under reduced pressure, the residue redissolved in 1,4-dioxane/H2O (5 mL, 1:1) and the solution cooled to 0° C. NaHCO3 (150 mg, 1.77 mmol) and Fmoc-OSu (220 mg, 0.650 mmol) were added and the reaction was stirred overnight at room temperature. The 1,4-dioxane was removed under reduced pressure, the aqueous residue washed with hexane, then acidified with HCl (1M aqueous solution) and extracted with EtOAc. Column chromatography over SiO2 afforded the desired product as a colorless solid.

MS (ESI): found 377.1 [M+H]+, calculated 377.1 [M+H]+

Example 3

Synthesis of (3):
Fmoc-N-Pyrrolo-Alanine-Pentafluorophenyl Ester

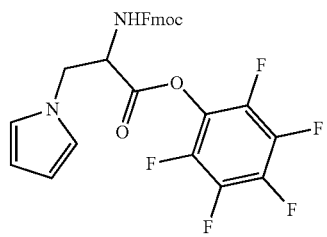

(3)

A solution of Fmoc-N-Pyrrolo-alanine (2) (100 mg, 0.267 mmol) in DMF (2 mL) and diisopropylethylamine (DIPEA) (93 μL, 0.534 mmol) was cooled to 0° C. Pentafluorophenyl-trifluoroacetate (50 μL, 0.292 mmol) was added and the reaction was stirred for 1 h at room temperature. Sat. aq. NaCl solution (15 mL) was added and extracted with EtOAc (3×30 mL). The combined organic layers were dried over Na2SO4 and purified by SiO2 column chromatography (hexane/EtOAc=4:1) affording the desired product (58 mg, 40%) as a colorless solid.

MS (ESI): found 543.1 [M+H]+, calculated 543.13 [M+H]+

Example 4

Synthesis of (4):
5'-Pyrrolo-alanine-aminohexanol-T10-3'

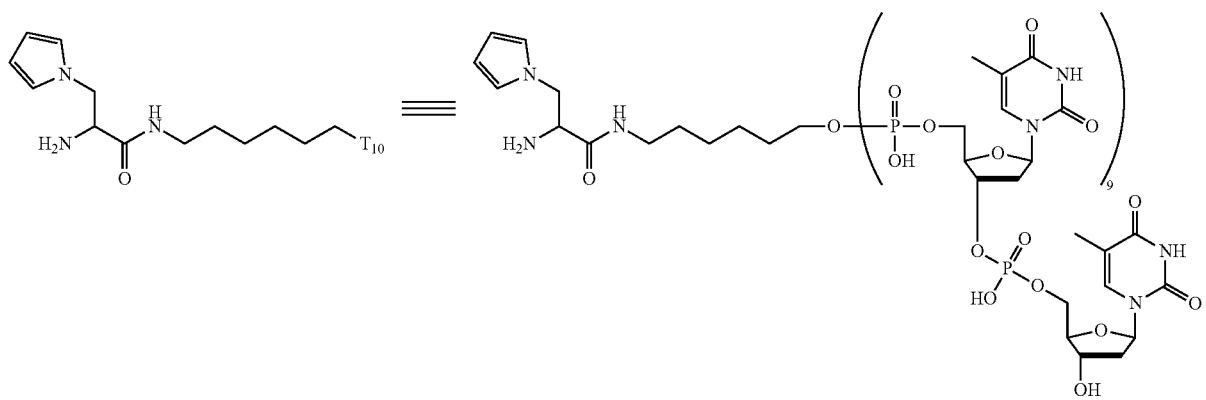

(4)

A 5'-aminohexanol-T10-3 oligonucleotide (80 μL, 2.15 mM in H2O, 172 nmol; synthesized according to classical oligonucleotide synthesis procedures) was added to sodium borate buffer (250 μL, pH=8.5, 0.1M). Subsequently Fmoc-N-Pyrrolo-alanine-pentafluorophenyl ester (3) (150 μL, 10 mM in MeCN, 1500 nmol) was added. After 2 h shaking at room temperature diethylamine (100 μL) was added to the solution, which was shaken for additional 30 minutes. Syringe filtration and dialysis afforded the desired product (120 nmol, 70%).

MS (ESI): found 1097.3 [(M−3H)/3]−

Example 5

Synthesis of (5): 4-Formylbenzoate NHS-Ester

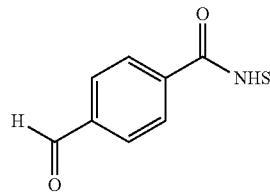

(5)

To a solution of 4-Formylbenzoic acid (1.00 g, 6.66 mmol) in DMF (30 mL) were added EDC-HCl (1.40 g, 7.33 mmol) and N-hydroxysuccinimide (842 mg, 7.33 mmol). After stirring for 16 h at room temperature the mixture was diluted with EtOAc (150 mL) and washed with sat. aq. NaCl solution (3×50 mL). The organic phase was dried over Na2SO4 and the solvent removed affording the desired product (1.40 g, 5.66 mmol, 85%) as a colorless solid.

1H NMR (CHLOROFORM-d, 400 MHz): δ=10.13 (s, 1H), 8.21-8.37 (m, 3H), 7.96-8.07 (m, 3H), 2.93 ppm (d, J=8.7 Hz, 6H)

Example 6

Synthesis of (6): 4-Formylbenzamido-undecanol-hexaphosphate-2'-deoxycytidine

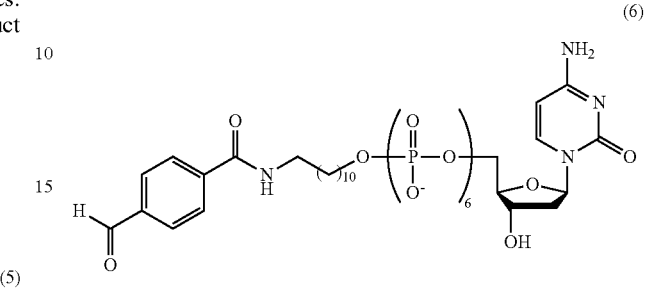

(6)

Amino-undecanol-hexaphosphate-2'-deoxycytidine (synthesized according to Fuller et al., PNAS, 113, 5233) (714 μL, 5.6 mM in H2O, 4 μmol) and 4-formylbenzoate NHS-ester (5) (800 μL, 50 mM in MeCN, 40 μmol) were added to sodium borate buffer (500 μL, pH=8.5, 0.1M). After 3 h shaking at room temperature the reaction mixture was purified by reversed phase chromatography (0-35 MeCN in H2O, 0.1 M triethylammonium acetate) affording the desired product (1.82 μmol, 46%).

MS (ESI): found 522.2 [(M−2H)/2+38]−, 1045.3 2 [M−H+38]−

Example 7

Conjugation of 4-Formylbenzamide-undecanol-hexaphosphate-2'-deoxycytidine (6) with 5'-Pyrrolo-alanine-aminohexanol-T10-3' (4)

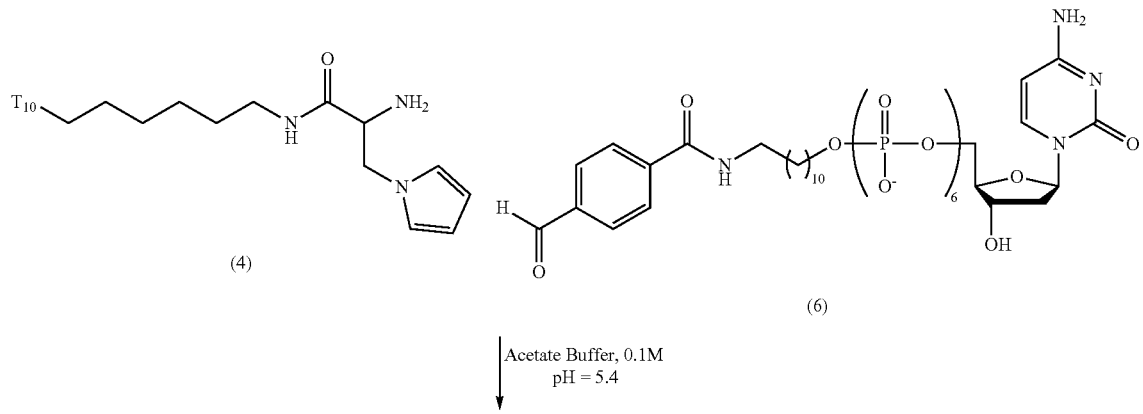

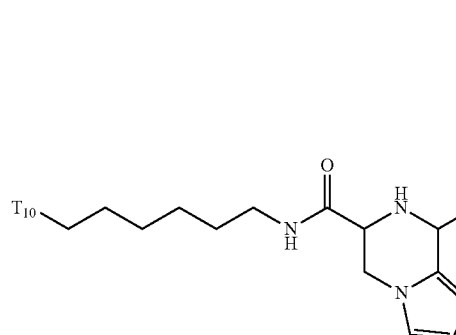
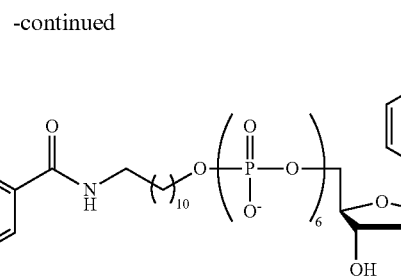

(7)

To an acetate buffer (0.1 M, pH=5.4, 50 μL) 5'-Pyrrolo-alanine-aminohexanol-T10-3' (4) (30 μL, 1.2 mM in H2O) and 4-Formylbenzamide-undecanol-hexaphosphate-Cytidine 2' deoxycytidine (146) (10 μL, 3.6 mM in H2O) were added, and the mixture was shaken at 37° C. for 16 h obtaining a nearly complete conversion of the substrates to the desired cyclized conjugate (87). hexaphosphate-2'deoxycytidine (6) (10 μL, 3.6 mM in H2O) were added, and the mixture was shaken at 37° C. for 16 h obtaining a nearly complete conversion of the substrates to the desired cyclized conjugate (7).

MS (ESI): found 1439.7 [(M−3H)/3]−+38

In this example the feasibility of the Pyrrolo Pictet Spengler reaction for the conjugation of oligonucleotide/nucleotide building blocks is demonstrated. In a stoichiometric 1:1 reaction at a concentration of 0.4 mM LCMS shows a nearly quantitative conversion of the substrates to the conjugation product within 16 hours.

Example 8

Synthesis of 8: 4-(1,3-dioxolan-2-yl)-N-(11-hydroxyundecyl)benzamide

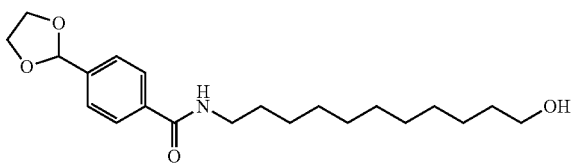

(8)

4-(1,3-dioxolan-2-yl)benzoic acid (1.05 g, 5.4 mmol) was dissolved in 12 mL dry DMF. DIPEA (1 mL, 5.94 mmol) and HATU (2.25 g, 5.9 mmol) were added and stirred at room temperature for 15 mins. A yellowish/orange solution was formed. A solution of 11-amino-1-undecanol (1.26 g, 6.7 mmol) and DIPEA (466 μL, 2.7 mmol) in 5 mL DMF was added. This solution was allowed to stir for 3 h at room temperature. After addition of water an ivory colored precipitate was formed and afterwards isolated. Final purification was achieved by flash chromatography (EtOAc+1% NEt3). An off-white solid was obtained (1.6 g, 80%).

MS (ESI): found 362.2 [M−H]−, calculated 362.24 [M−H]−

$^{1}$H NMR (CHLOROFORM-d, 400 MHz): δ=7.77 (d, J=8.0 Hz, 2H), 7.53 (d, J=8.2 Hz, 2H), 6.22 (br s, 1H), 5.84 (s, 1H), 3.98-4.16 (m, 4H), 3.62 (t, J=6.7 Hz, 2H), 3.44 (q, J=6.8 Hz, 2H), 2.91-3.01 (m, 2H), 2.85-2.91 (m, 2H), 1.48-1.67 (m, 4H), 1.20-1.41 ppm (m, 14H)

Example 9

Synthesis of 9: 11-(4-formylbenzamido)undecylmonophosphate

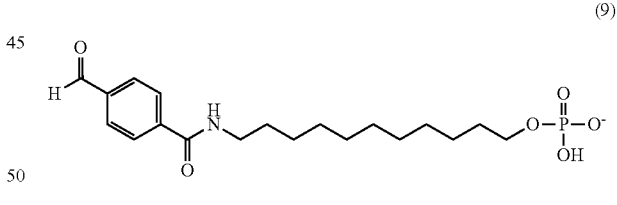

(9)

The alcohol 8 (1 g, 2.8 mmol) was dissolved under Ar in 40 mL THF (dry). To this solution triethylamine (692 μL, 5.0 mmol) was added and cooled to 0-4° C. in an ice bath. After addition of POCl3 (377 μL, 4.1 mmol) a white precipitate was formed immediately. The solution was allowed to come slowly to room temperature. After 150 min water was added until the precipitate was dissolved again. The solution was acidified to pH 1 by addition of 1 M HCl and allowed to stir at rt for 18 h. THF was evaporated and the crude product was purified by RP18 chromatography (water: MeOH). Yield (2.55 mmol, 93%) was calculated by UV/Vis absorption at 260 nm. (E=8700 Lmol$^{-1}$ cm$^{-1}$).

MS (ESI): found 398.2 [M−H]−, calculated 398.17 [M−H]−

$^{31}$P NMR (MeOD, 400 MHz): δ=0.17 (s, 1P)

Example 10

Synthesis of 10: 11-(4-formylbenzamido)undecyltriphosphate

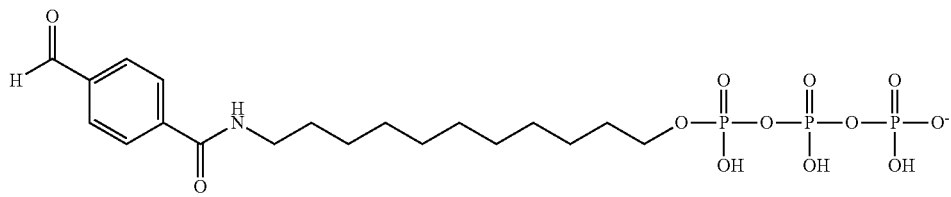

(10)

The monophosphate 9 (0.78 g, 2 mmol) was dissolved under Ar in dry DMF. CDI (0.95 g, 5.9 mmol) was added and the solution was stirred for 4 h. Excess of CDI was quenched by addition of MeOH (394 µmol, 9.8 mmol). After 30 min a solution of tributylammonium pyrophosphate (0.5 M in DMF, 7.8 mL, 3.9 mmol) was added and the solution was stirred for 18 h. A sticky precipitate was formed, that dissolved over time. The solution was evaporated, 20 mL 0.1 M TEAA was added and the crude product was purified by RP18-HPLC (A: 0.1 TEAA, B: MeCN). Fractions containing product were pooled and the solution was lyophilized Yield: 1.1 mmol (58%, UV-Vis detection)

MS (ESI): found 558.2 [M–H]$^-$, calculated 558.32 [M–H]$^-$ $^1$H NMR (DEUTERIUM OXIDE, 400 MHz): δ=9.94 (s, 1H), 7.77-8.04 (m, 4H), 7.71 (br d, J=8.4 Hz, 1H), 7.54 (br d, J=8.2 Hz, 1H), 3.90 (q, J=6.8 Hz, 2H), 3.32 (t, J=6.9 Hz, 2H), 1.49-1.60 (m, 4H), 1.22 (t, J=7.3 Hz, 14H), $^{31}$P NMR (DEUTERIUM OXIDE, 162 MHz): δ=–11.04 (dd, J=20.1, 17.1 Hz, 1P), –23.59 ppm (t, J=20.1 Hz, 1P)

Example 11

Synthesis of 11a-d: Aldehyde-C11-hexaphosphates (dN6P)

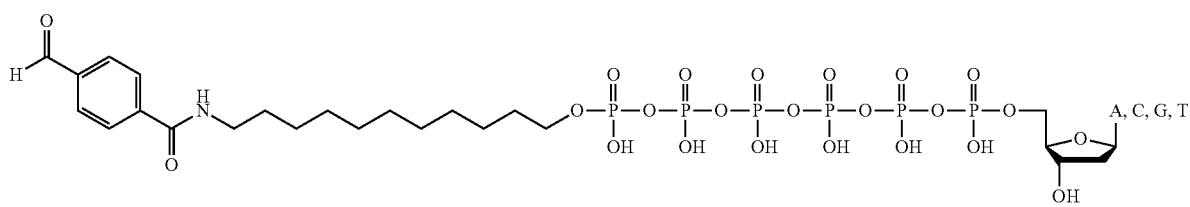

(11a-d)

The aldehyde-C11-triphosphate 10 (67 mg, 120 µmol) was dissolved under Ar in dry DMF. CDI (116 mg, 720 µmol) was added and the solution was stirred for 4 h. Excess of CDI was quenched by addition of MeOH (49 µmol, 1.2 mmol). After 30 min a solution of tributylammonium dNTP (0.08 M in DMF, 4.5 mL, 360 µmol) and magnesiumchloride (80 mg, 840 µmol) were added and the solution was stirred for 18 h. The solvent was removed and the residue was dissolved in 8 mL TEAA (0.1 M, pH 7). Final purification was carried out by RP18-HPLC (A: 0.1 TEAA, B: ACN,). Fractions containing product were pooled and the solution was lyophilized.

Typical yields: dA6P: 37%, dC6P: 51%, dG6P: 27%, dT6P: 72%

$^{31}$P NMR (DEUTERIUM OXIDE, 162 MHz): δ=−11.05 (d, J=17.1 Hz, 1P), −11.95 (d, J=17.1 Hz, 1P), −23.53-−21.40 ppm (m, 4P)

Example 12

General Procedure for the Synthesis of PyrAla-Oligonucleotide-Tags:

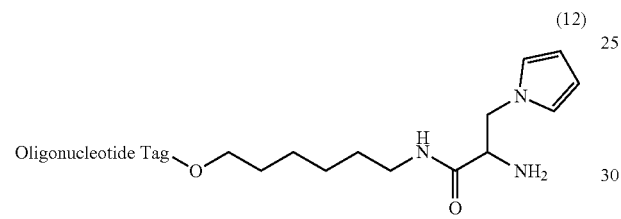

(12)

Amino-C6-Oligonucleotide was synthesized on an ABI394 DNA synthesizer on CPG solid support by phosphoramidite chemistry. A solution of Fmoc-PyrAla-PFP 3 (3 equivalents) and DIPEA (6 equivalents) in MeCN (50 mM and 100 mM respectively) was added to the CPG and shaken for 1 h at room temperature. The CPG was washed with MeCN and subsequently treated with 20% diethylamine in MeCN for 10 min. Cleavage from the solid support with conc. ammonia (on the synthesizer) and desalting via Vivaspin 3000K afforded the desired products in high purity (>90%) without any further purification.

Example 13

General Procedure for the Pictet Spengler Conjugation of PyrAla-Oligonucleotide-Tags With Aldehyde Functionalized Hexaphosphate-Nucleotides

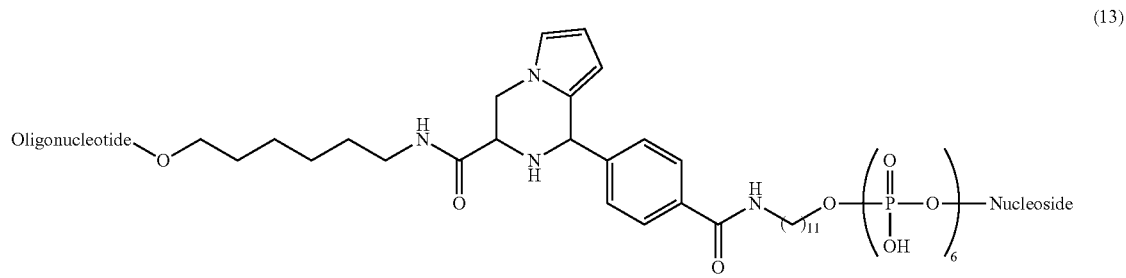

(13)

To lyophilized PyrAla-Oligonucleotide-Tag 12 were added aldehyde-hexaphosphate-nucleotide (10 mM in H$_2$O, 1 equiv) and acetate buffer (0.1 M, pH=5.3, reagent concentration: 1-5 mM). The solution was shaken for 24 h until complete conversion of the substrates to the Pictet Spengler cyclization product. Centrifugation in an Amicon 3k and purification with an X-Bridge preparative C18 HPLC column afforded the desired products (40-70%).

Example 14

General Procedure for the CuAAC Conjugation of Hexynyl-Oligonucleotide-Tags With Azido Functionalized Hexaphosphate-Nucleotides (14)

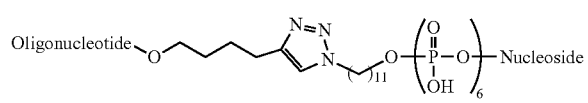

Hexynyl-Oligonucleotide-Tags were synthesized on an ABI394 DNA synthesizer on CPG solid support by phosphoramidite chemistry. An aqueous solution of the Hexynyl-Oligonucleotide-Tag and Azido-hexaphosphate-nucleotide (aqueous solution, 1.2 equivalents) were mixed; THPTA (0.1 M in H2O, 7.5 equivalents) and CuBr (0.1 M in DMSO/t-BuOH 3:1, 5 equivalents) were added to the solution, which was shaken for 1 h. Centrifugation in an Amicon 3k with EDTA and purification with an X-Bridge Preparative C18 HPLC column afforded the desired products (40-70%).

Example 15

Functional Comparison of Clicked Vs Pictet Spenger Conjugated Tag Sets via Sequencing on a Nanopore Sequencer:

A sequencing experiment (4 replicates of each condition) was performed with a Pol 6 type polymerase attached to a mutated alpha-Hemolysine nanopore embedded in a lipid bilayer on a fabricated electronic sensor microchip.

For the sequencing-by-synthesis reaction, a set of four 5'-tagged nucleoside hexaphosphates dT6P-(PAPS)-tag-1, dG6P-(PAPS)-tag-2, dA6P-(PAPS)-tag-3, and dC6P-(PAPS)-tag-4 synthesized with Pictet-Spengler chemistry (PAPS) according to example 13 was used. In a control experiment, a set of four 5'-tagged nucleoside hexaphosphates dT6P-(triazole)-tag-1, dG6P-(triazole)-tag-2, dA6P-(triazole)-tag-3, and dC6P-(triazole)-tag-4 assembled via a click chemistry (triazole) linker was used. Tags for each nucleoside residue were identical irrespective from the linker chemistry chosen.

For the sequencing reaction nucleosides were used in a concentration of 3 uM. The target sequence was pUC 2.7 kb. For the sequencing reaction, voltage was applied for a duration of 2700 seconds. Upon completion of the sequencing runs the sequencing data were analyzed using proprietary software analyses packages and the high quality reads (those with sufficient accuracy and reliable base call metrics) were aggregated from each condition to calculate procession length metrics. Procession rate was determined as the average of procession length divided by sequencing lifetime for each individual cell from the aggregated data.

For the Pictet Spengler conjugated nucleoside set, an average procession rate of about 2.35 bases/second was obtained, whereas with the click chemistry (triazole) conjugated nucleoside set, the average procession rate was about 1.7 bases/second.

The invention claimed is:

1. A method of sequencing a nucleic acid using a tagged nucleoside, wherein the tag has been linked to the nucleoside phosphate via a Pictet Spengler reaction, and the tagged nucleoside has the formula:

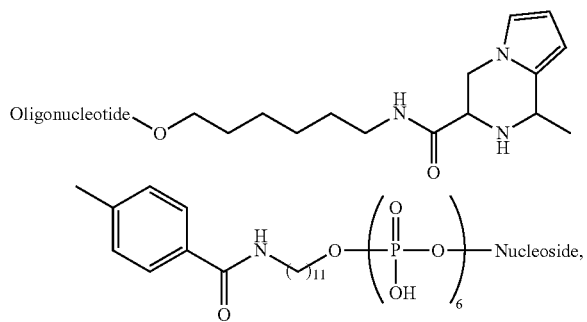

wherein the method comprises (i) adding the tagged nucleoside to a reaction chamber; (ii) carrying out a polymerization reaction with the aid of a polymerase, therby incorporating the tagged nucleoside into a complement of the nucleic acid, and (iii) detecting the identity of the tag by altered resistance, current, voltage, or capacitance.

2. The method according to claim 1, wherein the tag comprises a terminal N-(2-aminoethyl) pyrrole moiety has been linked to an aldehyde moiety connected via a linker to the 5'-end of a nucleoside phosphate.

3. The method according to claim 2, wherein the nucleoside phosphate is a nucleoside hexaphosphate.

4. The method according to claim 1, wherein the sequencing reaction is a sequencing by synthesis reaction.

5. The method according to claim 1, wherein the sequencing reaction is a single molecule sequencing reaction.

6. The method according to claim 5, wherein the sequencing reaction is a nanopore sequencing reaction.

7. The method according to claim 5, wherein the tag is a fluorescent tag.

* * * * *